US012501985B2

(12) United States Patent
Maiga

(10) Patent No.: US 12,501,985 B2
(45) Date of Patent: Dec. 23, 2025

(54) DEVICE, SYSTEM, METHOD AND KIT FOR IMPROVED SKIN CARE PRODUCT APPLICATION

(71) Applicant: Aminata H Maiga, Camp Springs, MD (US)

(72) Inventor: Aminata H Maiga, Camp Springs, MD (US)

(*) Notice: Subject to any disclaimer, the term of this patent is extended or adjusted under 35 U.S.C. 154(b) by 206 days.

(21) Appl. No.: 18/384,979

(22) Filed: Oct. 30, 2023

(65) Prior Publication Data

US 2024/0138542 A1 May 2, 2024

Related U.S. Application Data

(60) Provisional application No. 63/421,104, filed on Oct. 31, 2022.

(51) Int. Cl.
*A45D 34/04* (2006.01)
*A61M 35/00* (2006.01)

(52) U.S. Cl.
CPC ........... *A45D 34/04* (2013.01); *A61M 35/003* (2013.01); *A45D 2200/1081* (2013.01); *A45D 2200/207* (2013.01); *A45D 2200/25* (2013.01)

(58) Field of Classification Search
CPC ............ A45D 34/04; A45D 2200/1081; A45D 2200/207; A45D 2200/25; A61M 35/003; A61M 35/00
USPC ........................................ 401/6; 16/427, 429
See application file for complete search history.

(56) References Cited

U.S. PATENT DOCUMENTS 5,566,418 A * 10/1996 Steffen .................. A47K 7/028 D28/7
5,961,235 A * 10/1999 Kennedy ............... A45D 34/04 401/6
8,360,668 B1 * 1/2013 Hinnant .............. A46B 5/0075 401/6
2001/0053305 A1 * 12/2001 Berke .................... A45D 34/04 401/184
2003/0233718 A1 * 12/2003 Heathcock ............... B25G 3/16 15/144.4

* cited by examiner

*Primary Examiner* — David J Walczak
(74) *Attorney, Agent, or Firm* — Raymond Van Dyke; Van Dyke Intellectual Property Law

(57) ABSTRACT

Skin care tools, devices, apparatuses, systems, methods and kits to improve the application of compositions onto inaccessible surface areas, such as the middle part of the back. The instant invention has a handle for gripping at one end, and a shaped applicator at the other end, which is rounded and smooth on one side and flat on the other for contacting delicate surfaces, such as human skin, and evenly applying the therapeutics. In other embodiments, electronics are employed to facilitate the application of the liquids and provide more ease of use along with other functions.

18 Claims, 5 Drawing Sheets

DEVICE, SYSTEM, METHOD AND KIT FOR IMPROVED SKIN CARE PRODUCT APPLICATION

CROSS REFERENCE TO RELATED APPLICATION

The present invention is a nonprovisional of and claims priority to U.S. Provisional Patent Application Ser. No. 63/421,104, filed Oct. 31, 2022, entitled "DEVICE, SYSTEM, METHOD AND KIT FOR IMPROVED SKIN CARE PRODUCT APPLICATION," the disclosure of which is incorporated herein by reference.

FIELD OF THE INVENTION

The present invention is directed to improvements in techniques and equipment for individuals to apply moisturizers, sunscreens, medicinal rubs, lotions and other compositions to the middle of their backs, shoulders and other hard-to-reach body areas.

BACKGROUND OF INVENTION

The usage of lotions and moisturizers has grown, and the great diversity of such creams, sunscreens and other compositions has generated a wealth of such liquids, emulsions, admixtures, and other compositions for sale.

As demonstrated on a sunny day at the beach, nearly all humans have great difficulty applying compositions to particular areas of their body and ask others for help to apply compositions to those areas. For example, people have great difficulty directly reaching their upper middle back and shoulder areas, i.e., the arm/hand degrees of freedom do not permit most people to reach those areas, necessitating a third person to help, e.g., apply sunscreen.

Additionally, with age, one's flexibility decreases, making the inaccessible areas of the human body increase. Thus, the elderly, the disabled, the partially disabled, and others will have more areas out of reach.

With personal care products being a large industry, any improvements to increase usage of such compositions would satisfy a great need.

There is, therefore, a present need to provide an improved system, device, methodology or kit to improve a user's ability to apply compositions to their body, particularly to areas outside their reach.

SUMMARY OF THE PRESENT INVENTION

The present invention is directed to tools, devices, apparatuses, systems, methods and kits to improve the application of compositions onto inaccessible surface areas, such as the middle part of the back. The instant invention has a handle for gripping at one end, and a shaped applicator at the other end, which is rounded and smooth on one side and flat and smooth on the other for contacting delicate surfaces, such as human skin, and evenly applying the therapeutics. In other embodiments, electronics are employed to facilitate the application of the liquids and provide more ease of use along with other functions.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying DRAWINGS, where like reference numerals designate like structural and other elements, in which:

DETAILED DESCRIPTION OF THE PRESENT INVENTION

The present invention will now be described more fully hereinafter with reference to the accompanying DRAWINGS, in which preferred embodiments of the invention are shown. It is, of course, understood that this invention may, however, be embodied in many different forms and should not be construed as limited to the embodiments set forth herein; rather, these embodiments are provided so that the disclosure will be thorough and complete, and will fully convey the scope of the invention to those skilled in the art. It is, therefore, to be understood that other embodiments can be utilized, and structural changes can be made without departing from the scope of the present invention.

The present invention is generally directed to an improved apparatus, device, system, kit and technique for individuals to self-applicate hard-to-reach places, such as the middle of their backs, shoulders, and other such areas without needing assistance and not directly touching them.

The novel personal care device herein described is configured to allow individuals to apply moisturizing lotions, sunscreens, medicinal or therapeutic rubs, and similar products in an easier, more even, and less messy fashion than other such applicators in the prior art. The personal care device may also be of use to other individuals who may struggle to apply lotions, creams and such, i.e., the elderly, the disabled, or individuals recovering from surgery and having limited field of movement.

The personal care product depicted herein is primarily employed to reach the center of the back for application of moisturizing lotions and other such products. This "back" area rests between the shoulder blades to about the middle of the back, directly above the lower back. This is the area most people cannot reach without assistance. This area is approximately 10 to 12 inches square on adults, and around 8 inches square on children, such as a 12 year old. It should, of course, be understood that other body regions may also be unreachable to some, e.g., the obese or impaired.

Figures 1, 1A, 2, 3:
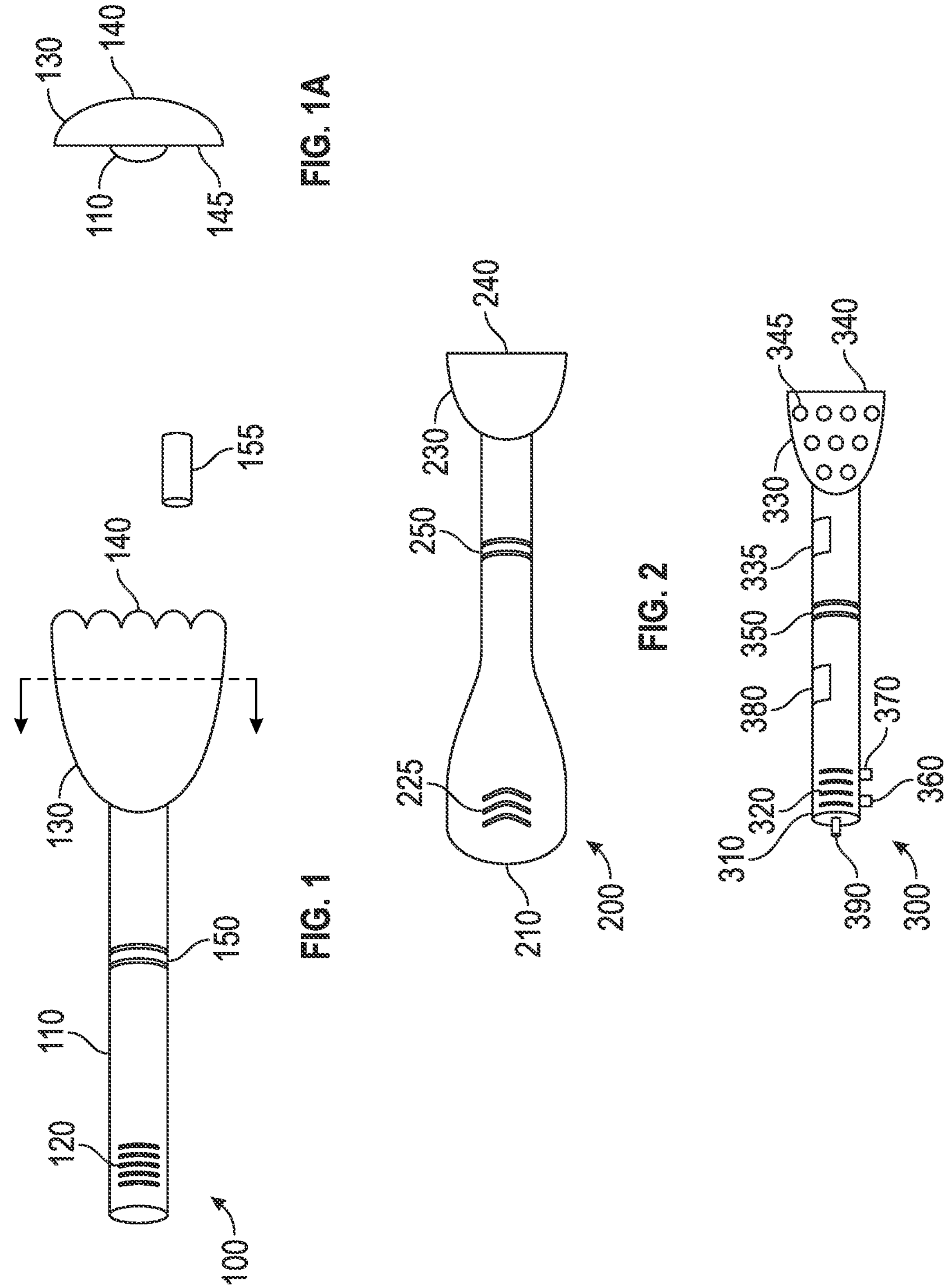
FIG. 1 is a representative view of a first skin care application device that may be employed using the principles of the present invention.
FIG. 1A shows a cross section view of the device in FIG. 1, showing the flat and rounded surfaces of the applicator.
FIG. 2 is a representative view of another skin care application device in another configuration that may be employed using the principles of the present invention.
FIG. 3 is a representative view of an electronic configuration of the skin care application device that may be employed using the principles of the present invention.

With reference now to FIG. 1 of the DRAWINGS, there is illustrated a representative configuration of a first embodiment of an improved skin care device practicing the principles of the present invention. The simple, flexible and versatile configuration shown, generally designated by the reference numeral 100, has a handle or handle portion, generally designated by the reference numeral 110, in this embodiment has a generally circular configuration to ensure a firm and good grip. The grip can be enhanced by the inclusion of materials to better secure the grip, generally designated by the reference numeral 120, and described further hereinbelow. It should be understood that the handle portion 110 in this embodiment may generally resemble the shape employed on hairbrushes.

Extending from the handle portion 110 is a shaft or extender portion or extender, generally designated by the reference numeral 150, terminating on the other end with an applicator, generally designated by the reference numeral 130, and preferably flat on one side and slightly rounded on the other, terminating with an edge or straight edge portion, generally designated by the reference numeral 140. The device 100 preferably reaches the middle of the back when the individual grasps the device 100 and guides it to the other end, using the aforesaid edge 140.

In an effort to better illustrate this applicator shape, with reference now to FIG. 1A of the DRAWINGS, there is illustrated a representative configuration of other end of the device 100, with a close section taken across the applicator portion 130 to best show the rounded area on one side and a flat area, generally designated by the reference numeral 145, on the other or obverse side, terminating with an edge or edge portion 140 having a rounded area. The rounded area of said edge portion 140 provides a smooth surface for the skin, but the flat portion 145 may provide a more targeted means to distribute or spread the applied lotions or even therapeutics over the desired areas.

It should be understood that the configuration 100 can be produced in a wide variety of materials and colors. In addition to inexpensive plastic versions, a more expensive version can be made of wood for the handle 110, and perhaps silicone for the rest of the shaft, as discussed in more detail hereinbelow.

As also shown in FIG. 1, the shaft or extender 150 can be adjusted or extended, such as by inserting one or more extension portions or rings, generally designated by the reference numeral 155, to lengthen the device 100 and thus extend the reach of the device 100 in use. It should be understood that multiple such extensions or rings 155 can be inserted to further increase the reach of the device 100.

In usage, the desired moisturizing lotion, medicinal rub, sunscreen or other product would be spouted or placed onto the flat portion 145. The user then grasps the handle portion 110, along the grip 120, and the applicator portion 130 and the edge or straight edge portion 140 at the other end would then be pressed against the aforesaid areas, and through manipulation evenly distributes the applied product on the middle of the back, shoulders, feet, ankles, arms or any other hard to reach areas. In other words, the device 100 is simply wanded over the body.

The configurations shown herein are designed for convenience, ease of use, and are lightweight, as well as compact and portable in design. Further, the configurations are durable and reasonably priced as a consumer product. The devices provide the individual with a feeling of independence and would reduce the mess associated with the application of these skin care products, along with the associated greasy feelings.

The use of this invention helps eliminate dry or irritated skin, which can be painful, e.g., itch and burn. Even young people may have afflictions that could use the advantages of the present invention, e.g., dry skin or other skin ailments.

The configurations shown are also versatile, i.e., able to apply a wide array of products, such as moisturizing lotions, medicinal rubs, sunscreens and more. The devices shown herein, in al of the embodiments, can also have appeal to single individuals living alone, the elderly or anyone with physical limitations, such as the disabled, the partially disabled, the obese or even those with arthritis or a stiff arm.

With reference now to FIG. 2 of the DRAWINGS, there is illustrated a representative configuration of another embodiment of an improved skin care device practicing the principles of the present invention. The simple, flexible and versatile configuration shown, generally designated by the reference numeral 200, similar to a spatula shape, which has a different handle portion 210, with a different end or grip portion 120, along with a different or perhaps the same gripping means thereon, generally designated by the reference numeral 225. An applicator or applicator portion 230 and the rounded area or portion thereof 240 in this embodiment may also differ in structure, with the edge or edge portion 240 thereof with a straight edge. In addition to manufacturing ease, this embodiment also provides a different mechanism to apply skin care products which some users may prefer. As shown and as discussed hereinabove, extenders 250 may be employed to adjust the length of the device 200.

With reference now to FIG. 3 of the DRAWINGS, there is illustrated a representative configuration of another embodiment of an improved skin care device practicing the principles of the present invention. This more advanced, yet flexible and versatile configuration shown, generally designated by the reference numeral 300, may have the same handle portion as 110/210, or a different one, generally designated by the reference numeral 310. Likewise, the same or a different end or grip portion, along with a different or perhaps the same gripping means thereon, generally designated by the reference numeral 320. An applicator or applicator portion 330 and the aforementioned edge or edge area 340 in this embodiment may also differ in structure, as described below.

For example, as shown in FIG. 3, the applicator 330 has a number of holes or pores, generally designated by the reference numeral 345, through which the desired therapeutic fluid would flow, i.e., from within reservoirs within the device 300, generally designated by the reference numeral 335.

The device 300 may further include a mode button, generally designated by the reference numeral 360, which could transition the device between one, two or more modes, e.g., including a vibratory mode and a massage mode, thereby providing additional therapeutic benefit to the use of the present invention. As the device 300 has power, the device can be turned on or off using a power button, generally designated by the reference numeral 370. To power the portable device, a battery compartment, generally designated by the reference numeral 380, along with a charge port, can provide sufficient power for a usage, and due to proper construction and shielding, all electronic components would be protected from moisture (as well as the user being protected from a short or other mishap).

It should be understood that the devices shown herein can be produced from a number of rigid medium- to lightweight plastic formulations, such as polystyrene, vinyl resins (including polyvinyl chloride), or polypropylene. As is understood in the art, these materials generally have good colorability, are reasonably priced, and are readily fabricated using a number of different manufacturing processes, including injection molding.

Whereas in the embodiments shown in FIGS. 1 and 2, the lotion or other liquid is slavered on the applicator 130/230, particularly the flat surfaces thereof 145, and then manually manipulated by the user into the skin of the desired areas For the lotion or other therapeutic in the embodiment of FIG. 3, stored in the reservoirs 335, the user here would press a button, generally designated by the reference numeral 390, to force some of the liquid from the reservoirs 335 and through the aforesaid pores 345 and unto the skin, where the user could then knead or otherwise work the liquid over the skin area, as above. It should also be understood that the button 390 could be graduated, i.e., the more you press, the more lotion or other liquid comes out, perhaps squirting out, providing a means to better satisfy some users desiring more liquid than most (or less conversely).

Figure 4A:
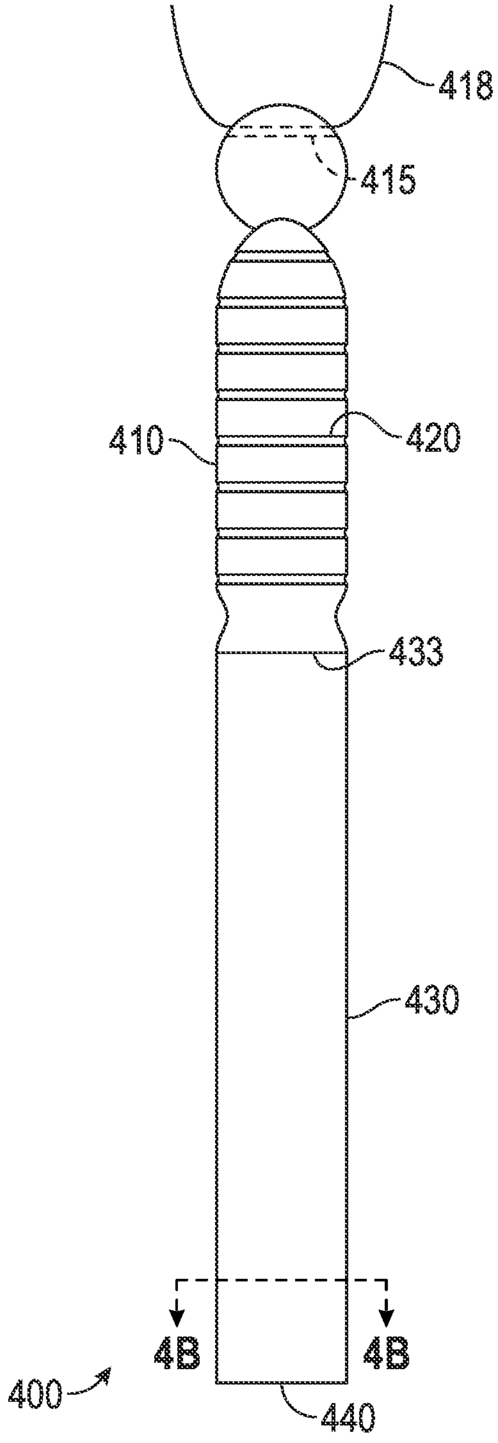
FIG. 4A illustrates another embodiment of a skin care device employing the principles of the present invention.
Figure 4B:
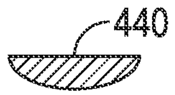
FIG. 4B shows a cross-section view of the device in FIG. 4A, illustrating the flat and curved surfaces of the applicator.

With reference now to FIG. 4, particularly to FIGS. 4A and 4B of the DRAWINGS, there is shown another embodiment of the instant invention, generally designated by the reference numeral 400. As shown in FIG. 4A, the device 400 includes a handle portion 410 with a number of striations or grooves along the surface forming a gripping mechanism 420 for better handling during use.

The handle or handle portion 410 in this embodiment also includes a hole at the top, generally designated by the reference numeral 415, through which a rope or ribbon is threaded, generally designated by the reference numeral 418, which provides a way to hang the tool 400 on a hook or other such means for storage when not in use. Another use for the rope 418 is to further assist in the use of the device 400, i.e., the user wraps the rope 418 around their hand to help in a better grip and control.

The device 400 also includes an applicator portion 430 and an edge or edge portion 440, by way of which a lotion, sunscreen, therapeutic or other liquid, emulsion or other solution may be applied to the skin, e.g., long the portion of the back inaccessible to most humans.

With reference now to FIG. 4B, similar to FIG. 1B, the applicator portion 430 in this cross-section best shows the rounded area on one side and a flat area on the other.

It should be understood that the compositional materials of the instant invention, as shown in the various embodiments, can be wood, such as balsa wood, plastic, silicone, a wood/silicone composite, as discussed hereinabove, and other materials as is understood to one of skill in the arts. For example, in one such embodiment, the entire device 400 is made of wood, and carved out of a single piece of wood. It should, of course, be understood that the handle portion 410 and the applicator portion 430 could instead be two separate components joined together along a seam, generally designated by the reference numeral 433, which could also conjoin different materials together. It should also be understood that a large number of wood types are possible in this construction, as well as combinations with silicone and other substances.

In a preferred embodiment, such as shown in FIG. 4, the dimensions of the parts may differ for adults and children, e.g., children approximately nine or so years of age and more, as well as for smaller adults. Likewise, the diameters of the handle portion can vary to best accommodate a user.

In an adult configuration, the preferred length dimension for the handle portion 410 is about 3 to about 6 inches, about 3 to about 5 inches, and most preferred about 4 inches, and the applicator portion 430 is about eight to nine inches. In a child configuration, the handle portion 410 is about 3 three inches, and the applicator portion is about six inches. Thus, for children, the entire device 400 is about 9 inches long, and in adults about 12-13 inches long. It should, of course, be understood that variations of these dimensions are possible.

Figure 5A:
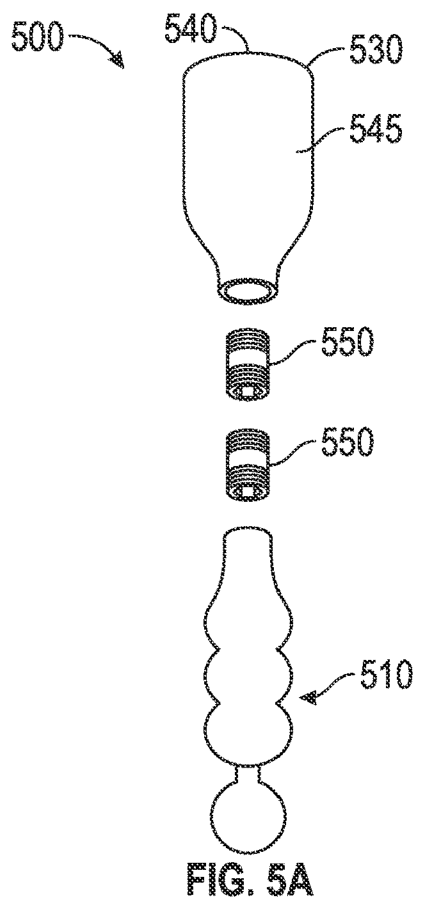
FIGS. 5A and 5B illustrate front and side views, respectively, of another embodiment of the present invention in a disassembled state.

With reference now to FIGS. 5A to 5D of the DRAWINGS, there is shown another embodiment of the present invention. With reference to FIG. 5A, there is shown a device, generally designated by the reference numeral 500, shown in a front view with the components thereof in a disassembled state. As with the other embodiments, the device 500 has a handle, generally designated by the reference numeral 510, which is designed or configured to allow the user to firmly grasp the device 500 during use, e.g., the user gripping the device 500 can self apply lotions, sunscreens or salves to their own back. Although a particular configuration of this handle 510 is shown, it should be in understood that additional gripping means 225, may be applied to further improve the user's grip. It should also be understood that alternate configurations of the handle 510 are possible. In any event, although the handle 510 must be functional for the purpose of the invention, it could, of course, be ornamental as well.

Also shown in FIG. 5A is an applicator, generally designated by the reference numeral 530, onto which the aforesaid lotions, sunscreens, ointments of other liquids, gels, emulsions or compositions are deposited, and then, employing the handle 510, the user applies the deposit to their back or other body portion, as described. For example, the lotion could be deposited onto a flat portion of the device, generally designated by the reference numeral 545 as shown, of the applicator 530, and applied. The applicator 530 also has a rounded portion and an edge area, generally designated by the reference numeral 540, described further hereinbelow, by which the user can evenly (or otherwise) distribute the lotions or gels, e.g., by working it onto the surfaces of their back.

It should, of course, be understood that the device 500 should comprise all smooth surfaces and rounded edges to facilitate the use of the invention and avoid discomfort or pain. For example, the edge or edge portion 540 is both straight and smooth.

With further reference to FIG. 5A, there is shown a plurality of extenders, each generally designated by the reference numeral 550, which connect together and to the handle 510 and applicator 530. In this embodiment, the extenders 550 include screw threads or other detachable interlocking means, e.g., the components screw or otherwise interlock together, forming a strong connection needed for the operation of the device 500. It should be understood that although threads are illustrated in this embodiment, male threads at one end and female at the other, additional or alternate interlocking means, such as the telescoping means shown in connection with FIG. 6 hereinbelow, are contemplated.

Figure 5B:
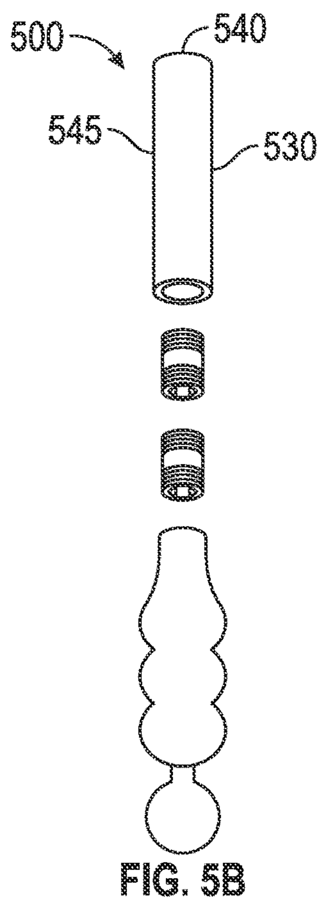

With reference now to FIG. 5B of the DRAWINGS, the disassembled components of the device 500 are shown in profile or at the side. The handle 510 profile in this configuration is the same in this view as that shown in FIG. 5A, but, as discussed, variations in the handle 510 and the grip aspects can be implemented. As shown, the applicator 530 in this embodiment is substantially flat, e.g., there are two of the aforementioned substantially flat surfaces 545 in this embodiment. Of course, in an alternate embodiment there may be only one such flat surface 545 with the other side more rounded (and smooth), e.g., a shaped applicator 530 configured to include the aforesaid reservoirs 335, and other mechanisms to store and deliver the liquids contained therein, such as through the aforementioned holes or pores 345 and activated using a mode button 360 (perhaps with vibratory or massage motion included) and an applicator button 390 to eject the liquids in a controlled manner.

Figure 5C:
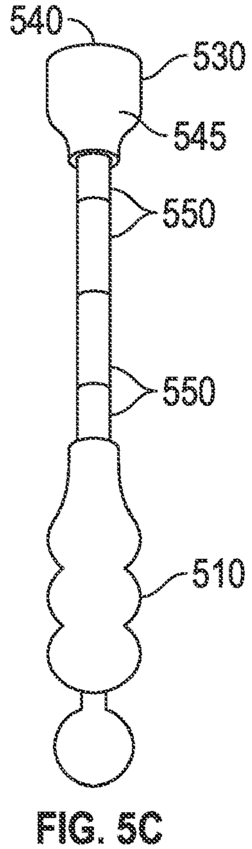
FIGS. 5C and 5D illustrate front and side views of the embodiment shown in FIGS. 5A and 5B, respectively, of the present invention in an assembled state and including additional extenders, FIG. 5D also illustrating the components in cross section.
Figure 5D:
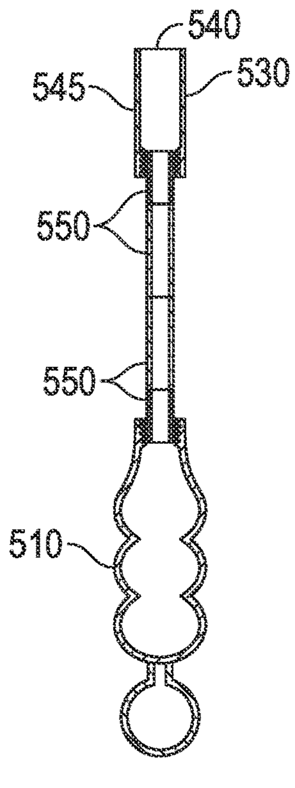

With reference now to FIGS. 5C and 5D, there are shown in the aforedescribed components of the device 500 now assembled and ready for use in the aforementioned front and side views, respectively. With reference now to FIG. 5D, the device 500 is also shown in cross section, and various threaded interconnections shown, described in more detail hereinbelow. As shown, at respective ends of the handle 510 and the applicator 530, the extenders 550 extend into these components, e.g., into respective cavities with threaded sides to threadably engage with respective extenders 550 as shown. It should be understood that the extenders 550 firmly engage the threads in the cavities of the handle 510 and applicator 530, anchoring these two components to a common arm.

Although in this embodiment each extender 550 is the same size, i.e., each of said plurality of extender components being identical, it should be understood that variable length extenders 550 may be employed in this and other embodiments, e.g., a kit or other portable carrier configured to house the device 500 components, such as in the disassembled state shown in FIGS. 5A and 5B, will include sufficient numbers and sizes of the interlocking extenders 550 to accomplish multiple uses. Likewise, each of said plurality of extender components may vary in diameter, such as in the kit embodiment.

Since a variable number (and size) of extenders 550 may be used, the device 500 is thus adjustable in length for use by children and adults, e.g., children perhaps as young as nine years of age. Thus, this interchangeability creates advantages for all family uses.

Thus, two, three, four or more extenders 550 may be used for this expandability, with the ranges being 1 to 6, 2 to 5, 3 to 4.

In a preferred embodiment, the device 500 includes a group of extenders 550, also termed an arm, such as composing three or four extenders 550. With four extenders 550, as illustrated in FIGS. 5C and 5D, the extenders can be all the same length, e.g., from about 2 inches to about 6 inches, about 3 inches to about 5 inches, and most preferably about 4 inches in longitudinal length. Radially, the extenders 550 are about 0.5 inch to about 2 inches, about ¾ inch to about 1.5 inch, and most preferably about 1 inch in radial length or diameter. As shown, two of the extenders 550 are deployed in the cavities of the handle 510 and applicator 530, as discussed, to a depth of about ¾ inch to about 2 inch, about 1 inch to about 1.5 inch, and most preferably about 1.25 inches, anchoring the components at a junction or conjunction, as shown. As discussed, the extenders 550 threadably engage within the respective cavities, anchoring the handle 510 or applicator 530 at a conjunction point. Thus, in this embodiment, with 4 inch extenders and 1.25 inch cavity depth, the arm is about 13.5 inches long. With fewer (or more) extenders 550 or where variable size extenders 550 are employed, the arm length can be adjusted.

Accordingly, a user grasping the device 500 by the handle 510, obtaining a good grip thereof, can reach around themselves and maneuver the device 500, particularly the smooth applicator 530 portion (with sunscreen et al. applied to the flat surface 545 and kneaded using the rounded area 540) onto their back, particularly hard to reach portions such as the middle of the back, as described.

Alternatively, employing the buttons and reservoirs previously described, the user may deploy the applicator 530 onto their back and then initiate the aforementioned lotion dispenser or delivery mechanism (reservoirs and pores) to have the lotion or sunscreen mechanically or electronically applied to their back. The user then kneads and spreads the lotion across their back using the rounded edge 540 of the applicator 530, and delivers more lotion as desired.

With regard to the applicator 530, in addition to this component being rounded and smooth on all sides for contacting delicate surfaces, such as human skin, the applicator 530 must evenly distribute or apply the lotion, sunscreen or therapeutics. Accordingly, the aforesaid edge area or edge 540 is configured as a thin edge that can help scrape off excess lotion from one area of skin for use elsewhere, as also described hereinabove.

Figure 6A:
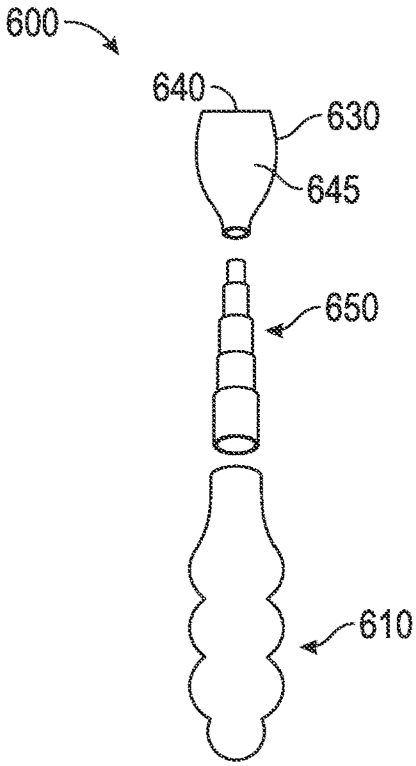
FIGS. 6A and 6B illustrate front and side views, respectively, of another and presently preferred embodiment of the present invention in a disassembled state.

With reference now to FIGS. 6A to 6E of the DRAWINGS, there is shown another and presently-preferred embodiment of the present invention, also in a disassembled state. With reference to FIG. 6A, there is shown a device, generally designated by the reference numeral 600, shown in a front view with the components thereof disassembled. As with the other embodiments, the device 600 has a handle, generally designated by the reference numeral 610, which is designed or configured to allow the user to firmly grasp the device 600 during use, e.g., the user applying lotions, sunscreens or salves to their own back, as described.

In this alternate embodiment of the present invention, the aforesaid extender, generally designated by the reference numeral 650, is instead of a number of interlinking components is a unitary telescoping construction or device, with gradations for positions, i.e., in a minimal configuration (the extender 650 maximally compressed), the device 600 is shortest, e.g., for use by a child. In a maximal configuration (fully extended), the extender or arm 650 of the device 600 would be the longest. Intermediate positions include a number of stepped positions or sizes that lock (interlock) into a particular desired position or length for use. Of course, the telescoping extender 650 is configured to be conveniently unlocked for positioning in other lengths. Further, the extender 650 becomes affixed with the aforesaid cavities at the juncture therebetween.

In this configuration, the aforementioned kit of components would be three. The detachable handle portion 610, the detachable applicator 630 and the arm 650, which is snugly or affixably deployed into respective cavities within the handle 610 and applicator 630, similar to the anchoring done and as set forth at length in the previous embodiment.

Figure 6B:
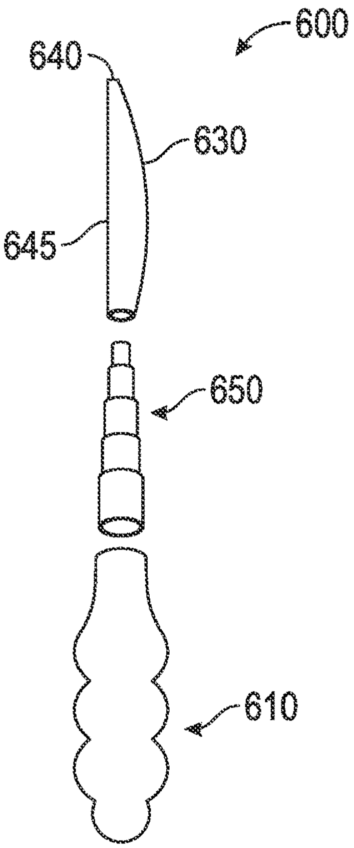
Figure 6C:
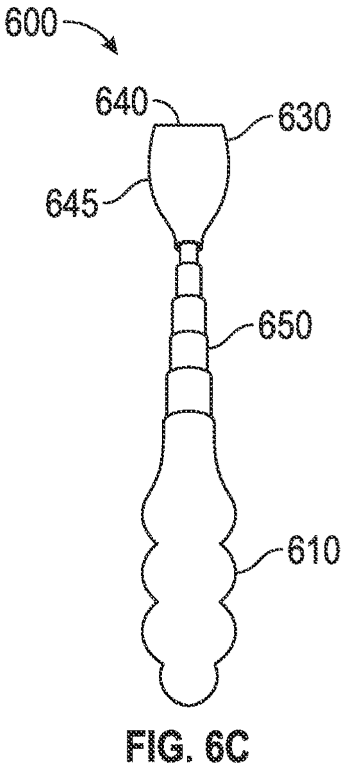
FIGS. 6C and 6D illustrate front and side views of the embodiment shown in FIGS. 6A and 6B, respectively, of the present invention in an assembled state.
Figure 6D:
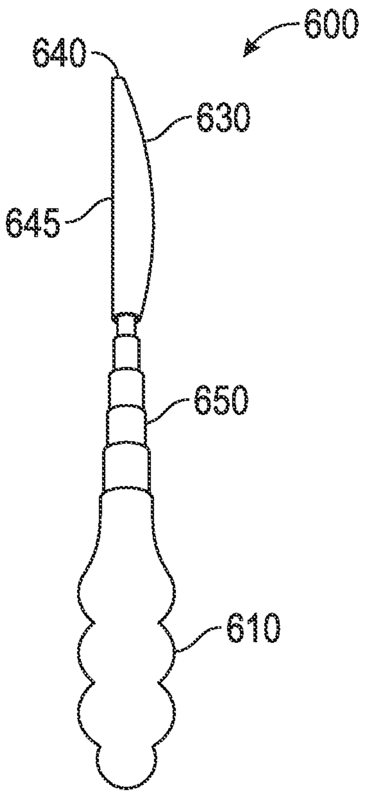
Figure 6E:
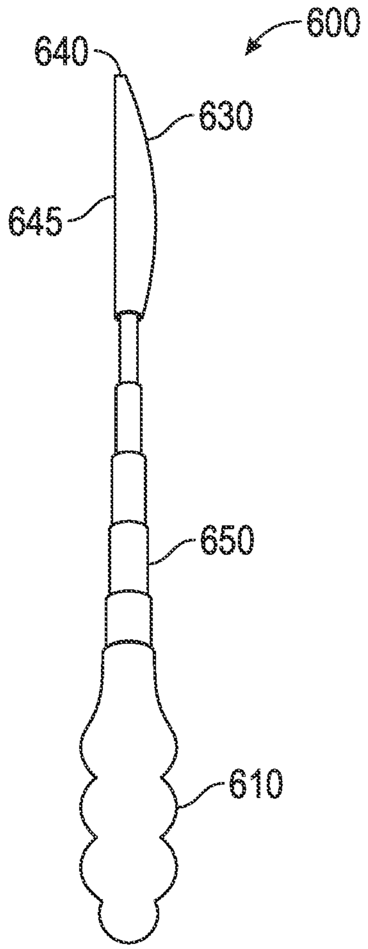
FIG. 6E illustrates an assemblage of components such as shown in FIG. 6D, but with the extender at maximum.

With reference now to FIGS. 6C and 6D of the DRAWINGS, the three components are shown, in front view and in side view, respectively, in an assembled state. For example, the telescoping extender 650 shown here is in a minimal state, i.e., not fully extended. With reference now to FIG. 6E, extender 650 is shown in a maximal state, i.e., compare FIGS. 6D and 6E.

In a currently preferred alternate configuration, the overall length of the device 600 varies from about 15 to about 26 inches. For example, the handle 610, as shown in FIGS. 6A and 6C, has a preferred height of about 4 to about 7 inches, about five to about 6 inches, and most preferably about 6 inches. As discussed, ornamental features can be added here, along with other features, such as a rope or ribbon 418 described hereinabove in more detail.

The applicator or head 630 can have a height of about 3 to about 5 inches, about 3.5 to about 4 inches, and most preferably 3.75 inches. In a currently preferred configuration or shape, the applicator 630, as shown in FIGS. 6A and 6C, is about 2.2 to about 2.8 inches in width, about 2.4 to about 2.7 inches, and most preferably about 2.6 inches wide in the middle, which is the widest width in this embodiment. As shown at the top and bottom of the applicator 630, the width tapers to about 1.9 inches to about 2.3 inches, about 2 inches to about 2.2 inches, and most preferably about 2.1 inches. Of course, at the bottom portion of the applicator 630 the width tapers further toward the aforesaid connection points within the cavities therein, as illustrated and described in depth hereinabove. This shaped configuration has advantages over the other configurations shown, e.g., Applicant has found this configuration the most versatile for the various uses.

Finally, the adjustable extender 650 (or arm) has a preferred length of about 11 to about 13 inches. Of course, in this configuration, the ends of the extender 650 fit snugly within the aforesaid cavities of the handle 610 and applicator 630, making the assembly a firm and construction suitable for use. As discussed, the ends of the arm 650 may instead interlock into the respective cavities to anchor the extenders 650 to the components.

As mentioned, for the aforesaid kit, the components disassemble, as shown in FIGS. 6A and 6B (and also FIGS. 5A and 5B), but are readily reassembled for use. It should thus be understood that this ease of disassembly and detachment makes the devices 500 and 600 quite convenient for storage when not in use, e.g., traveling to a destination. Similarly, the embodiments shown in FIGS. 1-4 are also easily portable.

In preferred embodiments, the handles 510 and 610 and the applicators 530 and 630 (as well as the equivalent structures in other embodiments) are preferably made of wood, such as bamboo or balsa, or a plastic, such as silicone, or combinations thereof, such as a wooden handle and a silicone applicator. Again, the surfaces thereof are smoothed, and all edges rounded.

In another preferred embodiment of the present invention the extenders 550/extender 650 are made of light-weight aluminum. It should, of course, be understood that other metals and materials may be utilized here so long as those materials provide sufficient strength for the uses intended. For example, soft or brittle materials should not be employed due to the torsions and other stresses placed on the devices 100/200/300/400/500/600 during use. Also, the threaded connections in device 500 should include materials strong enough for the maintenance of the structural integrity of the device 500.

As with the embodiment described in connection with FIG. 5, although a particular configuration of this handle 610 is shown, it should be in understood that additional gripping means 225, may be applied to further improve the user's grip. It should also be understood that alternate configurations of the handle 610 are possible, the handle 610 can thus be functional and ornamental as well.

The instant invention shows exemplary configurations presently preferred. Additional configurations are possible and variations of the above are considered within the ambit of the present invention. In a kit embodiment, the device 100/200/300/400/500/600 may be sold along with the extenders, such as extensions 155 and 550 and/or 650, and a variety of therapeutics may be employed in using the invention. Also, in the electronic version, the kit can also include batteries, a charging cord or other such configuration, along with any spare parts, fuses or other components.

The previous descriptions are of preferred embodiments for implementing the invention, and the scope of the invention should not necessarily be limited by these descriptions. It should be understood that various alternatives and equivalents are encompassed herein. The scope of the current invention is defined by the following claims.

What is claimed is:

1. An applicator device for skin care comprising:

a handle, said handle having a gripping portion along one end and a first connection conjunction at the other end thereof;

an applicator, said applicator having one surface planar and having at one end thereof a smooth edge, said applicator at the other end having a second connection conjunction, wherein said applicator has a rounded area obverse to said one surface; and, a telescoping extender with a plurality of extender components, said plurality of extender components configured to interlock with each other, said telescoping extender configured to connect to said handle at said first connector connection conjunction and to said applicator at said second connection conjunction, wherein said telescoping extender has a plurality of positions, said positions being from a minimal extension state to a maximal extension state with at least one intermediate position therebetween, said telescoping extender configured to lock into a respective state.

2. The applicator device according to claim 1, wherein a number of said plurality of extender components employed are selected from the group consisting of one to six, two to five, and 3 to 4.

3. The applicator device according to claim 1, wherein each of said plurality of extender components are identical in length.

4. The applicator device according to claim 1, wherein said plurality of extender components vary in length, the lengths for each of said extenders being selected from the group consisting of 2 inches to 6 inches, 3 inches to 5 inches, and 4 inches.

5. The applicator device according to claim 4, wherein at least two of said plurality of extender components vary in length.

6. The applicator device according to claim 1, wherein said plurality of extender components vary in diameter, the diameter for each of said extenders being selected from the group consisting of 0.5 inches to 2 inches, 0.75 inches to 1.5 inches, and 1 inch.

7. The applicator device according to claim 1, wherein said telescoping extender is made of aluminum.

8. The applicator device according to claim 1, wherein said handle comprises a grip material.

9. The applicator device according to claim 1, wherein said handle has at least one hole therethrough along said one end thereof, whereby said applicator device can be strung.

10. The applicator device according to claim 1, wherein said handle is a length selected from the group consisting of 3 to 6 inches, 3 to 5 inches, and 4 inches.

11. The applicator device according to claim 1, wherein said handle and said applicator are made of a material selected from the group consisting of wood, balsa wood, balsa wood and silicone admixture, a plastic, a rigid medium-to lightweight plastic, polystyrene, vinyl resins, polyvinyl chloride, polypropylene, and combinations thereof.

12. The applicator device according to claim 1, wherein said applicator further comprises at least one fluid reservoir within, a plurality of pores therethrough, and interconnections therebetween within which fluid flows from said at least one reservoir through to said pores.

13. The applicator device according to claim 12, wherein said applicator is configured to initiate said fluid flow from said at least one reservoir through said pores by a release button on said device.

14. The applicator device according to claim 13, wherein said release button is a graduated button, whereby continued pressure on said release button increases the fluid flow.

15. The applicator device according to claim 1, wherein said applicator further comprises a mode button, said applicator is configured to initiate a vibration or massage motion by initiation of said mode button.

16. The applicator device according to claim 1, wherein said applicator has a longitudinal length selected from the group consisting of 3 to 5 inches, 3.5 to 4 inches, and 3.75 inches, wherein said applicator has a width along a middle portion thereof selected from the group consisting of 2.2 to 2.8 inches, about 2.4 to 2.7 inches, and 2.6 inches, and wherein above and below said middle portion said applicator has a width selected from the group consisting of 1.9 to 2.3 inches, about 2 to 2.2 inches, and about 2.1 inches.

17. A kit for skin care comprising:

at least one handle, each said at least one handle having a gripping portion along one end and a first connection conjunction at the other end thereof;

at least one applicator, each said at least one applicator having one surface planar and having at one end thereof a smooth edge, each said at least one applicator at the other end having a second connection conjunction, wherein said applicator has a rounded area obverse to said one surface; and, at least one telescoping extender with a plurality of extender components, said plurality of extender components configured to interlock with each other, said telescoping extender configured to connect to said handle at said first connector connection conjunction and to said applicator at said second connection conjunction, wherein said at least one telescoping extender has a plurality of positions, said positions being from a minimal extension state to a maximal extension state with at least one intermediate position therebetween, said telescoping extender configured to lock into a respective state.

18. A method for application of a skin care product, said method comprising:

positioning a configured applicator device onto a body part for a treatment, wherein said applicator device compromises at least one handle, each said at least one handle having a gripping portion along one end and a first connection conjunction at the other end thereof, at least one applicator, each said at least one applicator having one surface planar and having at one end thereof a smooth edge, each said at least one applicator at the other end having a second connection conjunction, wherein said applicator has a rounded area obverse to said one surface, and at least one telescoping extender with a plurality of extender components, said plurality of extender components configured to interlock with each other, said telescoping extender configured to connect to said handle at said first connector connection conjunction and to said applicator at said second connection conjunction, wherein said at least one telescoping extender has a plurality of positions, said positions being from a minimal extension state to a maximal extension state with at least one intermediate position therebetween, said telescoping extender configured to lock into a respective state; and initiating, by a release button depressing, the flow of fluid onto said body part, said applicator device configured to spread the fluid, wherein said release button is a graduated button, whereby continued pressure on said release button increases the fluid flow.

* * * * *